US008522976B2

(12) United States Patent
Holstein

(10) Patent No.: US 8,522,976 B2
(45) Date of Patent: Sep. 3, 2013

(54) SYSTEMS, DEVICES, AND METHODS FOR INCREASING CONSUMER ACCESS TO FIRST AID SUPPLIES

(75) Inventor: Michael Holstein, Clearwater, FL (US)

(73) Assignee: Tender Corporation, Littleton, NH (US)

( * ) Notice: Subject to any disclaimer, the term of this patent is extended or adjusted under 35 U.S.C. 154(b) by 0 days.

(21) Appl. No.: 13/344,487

(22) Filed: Jan. 5, 2012

(65) Prior Publication Data

US 2013/0175193 A1 Jul. 11, 2013

(51) Int. Cl.
*A61B 19/02* (2006.01)
*A61F 13/00* (2006.01)

(52) U.S. Cl.
USPC ........................................... 206/441; 602/57

(58) Field of Classification Search
USPC ..................... 206/440, 441; 602/57; 229/84; 221/58
See application file for complete search history.

(56) References Cited

U.S. PATENT DOCUMENTS

| 4,194,624 | A | 3/1980 | Spiegelberg | |
|---|---|---|---|---|
| 5,271,522 | A | 12/1993 | Ko et al. | |
| 5,685,833 | A | 11/1997 | Turngren | |
| 6,018,092 | A | 1/2000 | Dunshee | |
| 6,124,522 | A * | 9/2000 | Schroeder | 602/57 |
| 6,299,018 | B1 | 10/2001 | Kimbrell | |
| 6,662,967 | B2 * | 12/2003 | Roy | 206/441 |
| 6,796,429 | B2 * | 9/2004 | Cameron et al. | 206/440 |
| 6,918,488 | B2 | 7/2005 | Renhed | |
| 6,923,320 | B2 | 8/2005 | Grossman | |
| 7,445,142 | B2 * | 11/2008 | Salani et al. | 206/441 |
| 7,506,760 | B2 | 3/2009 | Grossman | |
| 7,521,586 | B2 | 4/2009 | Schroeder | |
| 7,581,657 | B2 | 9/2009 | Dickmann | |
| 7,644,818 | B2 | 1/2010 | Spoljaric | |
| 7,659,439 | B2 | 2/2010 | Grossman | |
| 7,683,235 | B2 | 3/2010 | Wendorf | |
| 7,753,240 | B2 | 7/2010 | Leoncavallo et al. | |
| 7,762,635 | B2 | 7/2010 | Spoljaric | |
| 7,766,166 | B2 * | 8/2010 | Cognome Dotta | 206/441 |
| 7,857,137 | B2 * | 12/2010 | Law et al. | 206/441 |
| 7,967,140 | B2 | 6/2011 | Grossman | |

FOREIGN PATENT DOCUMENTS

| WO | WO-04-000688 A1 | 12/2003 |
|---|---|---|
| WO | WO-2006-078200 A1 | 7/2006 |
| WO | WO-2006-078201 A1 | 7/2006 |

\* cited by examiner

*Primary Examiner* — Bryon Gehman
(74) *Attorney, Agent, or Firm* — McLane, Graf, Raulerson & Middleton, Professional Association

(57) ABSTRACT

Systems and dispensers, including methods of using the same, for dispensing bandages comprising: a dispenser body comprising a receiving surface with a first retention element and a hinged flap with a second retention element, wherein the hinged flap is foldable to overlay at least a portion of the receiving surface; and at least one bandage pack disposed on the receiving surface, wherein the bandage pack comprises at least one individually wrapped bandage; provided that when the hinged flap is folded to overlay the receiving surface, a first retention element reversibly interlocks with a second retention element thus securely retaining the at least one bandage pack.

19 Claims, 17 Drawing Sheets

SYSTEMS, DEVICES, AND METHODS FOR INCREASING CONSUMER ACCESS TO FIRST AID SUPPLIES

BACKGROUND OF THE INVENTION

Medical emergencies pose a serious and prevalent threat to society. According to the Centers for Disease Control and Prevention (CDC), Americans suffered 29.6 million non-fatal injuries in 2009 and 31.5 million non-fatal injuries in 2010. Over 2.3 million non-fatal injuries each year are cuts or punctures. Emergency departments in the United States average approximately 400 visits for each 1000 people every year. The CDC further reports that injuries in the home result in about 30% of all injury-related emergency department visits. The National Institutes of Health and the Mayo Clinic recommend immediately covering wounds such as cuts, scrapes, and punctures with a sterile bandage.

SUMMARY OF THE INVENTION

Effective first aid requires easy and rapid access to sterile dressings appropriate to cover, protect, and help stop bleeding from a variety of wounds such as cuts, scrapes, and punctures. Consumers should have ready, ubiquitous access to dressings, such as sterile bandages. Moreover, bandages should be dispensed in a way that allows uncomplicated application with one hand. Because many injuries occur in the home, bandage dispensers should be inexpensive, yet attractive to encourage consumers to place them in multiple, easily accessed locations throughout their homes. Accordingly, we have identified a long-felt and unmet need for a consumer bandage dispenser with an inexpensive to manufacture design effective to retain a variety of bandage packs such that individual bandages are dispensed clean and ready to apply. Such a dispenser should also be easily refilled when bandage packs are depleted.

In one aspect, disclosed herein are systems for dispensing bandages comprising: a dispenser body comprising a receiving surface with a first retention element and a hinged flap with a second retention element, wherein the hinged flap is foldable to overlay at least a portion of the receiving surface; and at least one bandage pack disposed on said receiving surface, wherein said bandage pack comprises at least one individually wrapped bandage; provided that when the hinged flap is folded to overlay said receiving surface, a first retention element reversibly interlocks with a second retention element thus securely retaining said at least one bandage pack. In some embodiments, a first retention element, a second retention element, or both pass through at least one bandage pack. In some embodiments, the interlocking results from a first retention element fitting into a second retention element or vice versa. In some embodiments, the dispenser body comprises one or more pairs of opposing retention elements such that when a hinged flap is folded to overlay the receiving surface, each first retention element aligns with and opposes a second retention element. In further embodiments, the system comprises 1-10 pairs of opposing retention elements. In still further embodiments, the system comprises 2 pairs of opposing retention elements. In still further embodiments, the system comprises 1 pair of opposing retention elements. In some embodiments, at least one pair of opposing retention elements passes through at least one bandage pack. In some embodiments, the system comprises 1-10 bandage packs. In further embodiments, the system comprises 2 bandage packs. In still further embodiments, the system comprises 1 bandage pack. In some embodiments, the system comprises a hinged flap corresponding to each bandage pack.

In further embodiments, each bandage pack comprises 3 to 50 individually wrapped bandages. In further embodiments, each bandage pack comprises one or more pre-formed openings for passage of retention elements. In further embodiments, the dispenser body is substantially box-shaped. In further embodiments, the flap is hinged by thin, flexible material. In some embodiments, each bandage pack comprises a rigid cover and a plurality of individually wrapped bandages, wherein the individually wrapped bandages are bound to each other and to the cover, wherein removal of an individual bandage from the pack causes the bound portion of the wrapper to be retained, thus freeing and partially exposing a bandage. In some embodiments, the individually wrapped bandages are bound to each other and to the cover along a bottom edge. In some embodiments, each bandage pack includes a pre-formed opening. In further embodiments, a pre-formed opening allows one or more elements of a bandage dispenser (e.g., retention elements, etc.) to pass through a pack to secure a pack to a receiving surface, thus retaining a pack in a dispenser. In some embodiments, each bandage pack comprises 3 to 50 individually wrapped bandages. In further embodiments, each bandage pack comprises 5 to 40 individually wrapped bandages. In still further embodiments, each bandage pack comprises 10 to 20 individually wrapped bandages. In some embodiments, the bandage packs are the same size. In other embodiments, the bandage packs are not the same size. In some embodiments, the bandage packs have sizes selected from: 72 mm wide×40 mm deep×107 mm long, 62 mm wide×40 mm deep×107 mm long, 60 mm wide×40 mm deep×107 mm long, 80 mm wide×27 mm deep×107 mm long, 80 mm wide×34 mm deep×107 mm long, and 80 mm wide×40 mm deep×107 mm long. In some embodiments, the individually wrapped bandages have sizes selected from: 45 mm×51 mm, 40 mm×10 mm, 76 mm×38 mm, 76 mm×25 mm, and 76 mm×19 mm. In some embodiments, the dispenser body further comprises a surface with pre-drilled holes to facilitate mounting the dispenser to a fixed surface. In some embodiments, the dispenser body further comprises a surface with adhesive to facilitate mounting the dispenser to a fixed surface.

In another aspect, disclosed herein are systems for dispensing individual bandages comprising: a dispenser body comprising a substantially rectangular receiving surface with one or more first retention elements; a hinged flap with one or more second retention elements, wherein the hinged flap is foldable to overlay at least a portion of the receiving surface such that each first retention element aligns with and opposes a second retention element; one or more third retention elements on a side opposite the hinged flap; one or more bandage packs disposed on said receiving surface, wherein each said bandage pack comprises a plurality of individually wrapped bandages, wherein removal of an individual bandage from said pack causes a portion of the wrapper to be retained, thus freeing and partially exposing the bandage; provided that when the hinged flap is folded to overlay the receiving surface each first retention element passes through a bandage pack and reversibly interlocks with a second retention element. In some embodiments, the interlocking results from a first retention element fitting into a second retention element or vice versa. In some embodiments, the system comprises 1-10 pairs of opposing retention elements. In further embodiments, the system comprises 2 pairs of opposing retention elements. In still further embodiments, the system comprises 1 pair of opposing retention elements. In some embodiments, the system comprises 1-10 bandage packs. In further embodiments, the system comprises 2 bandage packs. In still further embodiments, the system comprises 1 bandage pack. In some embodiments, the system comprises a hinged flap corresponding to each bandage pack. In some embodiments, each bandage pack comprises 3 to 50 individually wrapped bandages. In some embodiments, each bandage pack comprises one or more pre-formed openings for passage of retention elements. In some embodiments, the flap is hinged by thin, flexible material.

In yet another aspect, disclosed herein are bandage dispensers comprising: a bandage pack receiving surface with one or more first retention elements; and a hinged flap with one or more second retention elements, wherein the hinged flap is foldable to overlay at least a portion of the receiving surface such that each first retention element aligns with, opposes, and reversibly interlocks with a second retention element. In some embodiments, the bandage dispenser further comprises one or more third retention elements on a side opposite the hinged flap. In some embodiments, the first and second retention elements are adapted to retain one or more bandage packs by passing through an opening in said packs. In some embodiments, the interlocking results from a first retention element fitting into a second retention element or vice versa. In some embodiments, the bandage dispenser comprises 1-10 pairs of opposing first and second retention elements. In further embodiments, the bandage dispenser comprises 2 pairs of opposing first and second retention elements. In still further embodiments, the bandage dispenser comprises 1 pair of opposing first and second retention elements.

In yet another aspect, disclosed herein are methods of dispensing bandages comprising the step of: grasping and pulling an individually wrapped bandage to remove the bandage from a multi-bandage pack; wherein the bandage pack is securely retained by a dispenser body comprising a receiving surface with a first retention element and a hinged flap with a second retention element; provided that the hinged flap is folded to overlay the receiving surface and a first retention element is reversibly interlocked with a second retention element to secure the bandage pack. In some embodiments, the first retention element, the second retention element, or both pass through the bandage pack. In some embodiments, the interlocking results from a first retention element fitting into a second retention element or vice versa.

In yet another aspect, disclosed herein are methods of refilling a bandage dispenser comprising the steps of: unfolding a flap hinged to a dispenser body, wherein the dispenser body comprises a receiving surface; removing a depleted bandage pack from the receiving surface; placing a new bandage pack onto the receiving surface, wherein the bandage pack comprises at least one individually wrapped bandage; and refolding the hinged flap to overlay at least a portion of the receiving surface such that a first retention element on the receiving surface reversibly interlocks with a second retention element on the hinged flap securely retaining the bandage pack. In some embodiments, the first retention element, the second retention element, or both pass through the bandage pack. In some embodiments, the interlocking results from a first retention element fitting into a second retention element or vice versa.

DETAILED DESCRIPTION OF THE INVENTION

Figure 1:
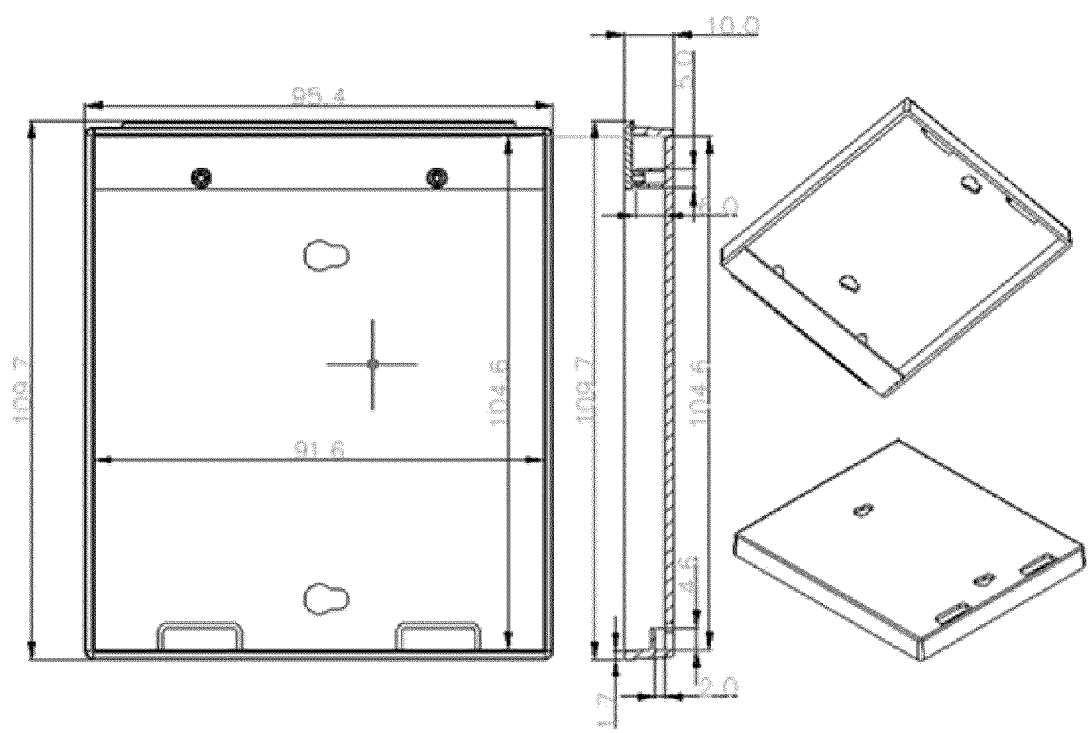
FIG. 1 shows multiple non-limiting views of an exemplary bandage dispenser; in this case, a bandage dispenser adapted to accommodate two bandage packs.

Existing first aid system designs are overly complex resulting in increased expense, consumer confusion, and potential for failures. Undue expense discourages ubiquitous access, reducing effectiveness in emergencies. Where designs fail, individual bandages are not dispensed cleanly or ready to apply to a wound. Complex bandage dispenser designs also discourage timely refilling of depleted bandage packs. Advantages of the methods, devices, and systems for dispensing individual bandages described herein include a cost-effective bandage dispenser design that encourages access, is easy to refill, and dispenses bandages in a clean and ready to apply state.

Accordingly, disclosed herein, in various embodiments, are systems for dispensing bandages comprising: a dispenser body comprising a receiving surface with a first retention element and a hinged flap with a second retention element, wherein the hinged flap is foldable to overlay at least a portion of the receiving surface; and at least one bandage pack disposed on said receiving surface, wherein said bandage pack comprises at least one individually wrapped bandage; provided that when the hinged flap is folded to overlay said receiving surface, a first retention element reversibly interlocks with a second retention element thus securely retaining said at least one bandage pack.

In various embodiments, provided are systems for dispensing individual bandages comprising: a dispenser body comprising: a substantially rectangular receiving surface with one or more first retention elements; a hinged flap with one or more second retention elements, wherein the hinged flap is foldable to overlay at least a portion of the receiving surface such that each first retention element aligns with and opposes a second retention element; one or more third retention elements on a side opposite the hinged flap; one or more bandage packs disposed on said receiving surface, wherein each said bandage pack comprises a plurality of individually wrapped bandages, wherein removal of an individual bandage from said pack causes a portion of the wrapper to be retained, thus freeing and partially exposing the bandage; provided that when the hinged flap is folded to overlay the receiving surface each first retention element passes through a bandage pack and reversibly interlocks with a second retention element.

Also disclosed herein, in various embodiments, are bandage dispensers comprising: a bandage pack receiving surface with one or more first retention elements; and a hinged flap with one or more second retention elements, wherein the hinged flap is foldable to overlay at least a portion of the receiving surface such that each first retention element aligns with, opposes, and reversibly interlocks with a second retention element.

Further disclosed herein, in various embodiments, are methods of dispensing bandages comprising the step of: grasping and pulling an individually wrapped bandage to remove the bandage from a multi-bandage pack; wherein the bandage pack is securely retained by a dispenser body comprising a receiving surface with a first retention element and a hinged flap with a second retention element; provided that the hinged flap is folded to overlay the receiving surface and a first retention element is reversibly interlocked with a second retention element to secure the bandage pack.

Disclosed herein, in various embodiments, are methods of refilling a bandage dispenser comprising the steps of: unfolding a flap hinged to a dispenser body, wherein the dispenser body comprises a receiving surface; removing a depleted bandage pack from the receiving surface; placing a new bandage pack onto the receiving surface, wherein the bandage pack comprises at least one individually wrapped bandage; and refolding the hinged flap to overlay at least a portion of the receiving surface such that a first retention element on the receiving surface reversibly interlocks with a second retention element on the hinged flap securely retaining the bandage pack.

Dispenser Body

In some embodiments, the methods, devices, and systems for dispensing individual bandages include a dispenser body. In further embodiments, a dispenser body includes a receiving surface with one or more first retention elements, one or more hinged flaps with one or more second retention elements, and one or more third retention elements. In still further embodiments, a hinged flap is foldable to overlay a receiving surface.

A dispenser body has many suitable shapes. In various embodiments, a dispenser body is, for example, rectangular, square, rhomboidal, hexagonal, octagonal, polygonal, oval, circular, irregular, or combinations thereof. In some embodiments, the shape of a dispenser body is chosen to accommodate the shape of a particular bandage and/or bandage pack. In other embodiments, the shape of a dispenser body is chosen to accommodate placement or mounting in a particular location.

In some embodiments, a dispenser body defines an interior compartment. In further embodiments, the interior compartment is box-shaped. In still further embodiments, the interior of the dispenser body defines a rectangular box-shape. In other embodiments, the interior of the dispenser body defines a square box-shape.

In some embodiments, a dispenser body includes a receiving surface. In some embodiments, a receiving surface is formed by the back wall of a dispenser body having an open box shape. In further embodiments, a receiving surface accommodates and contacts one or more bandage packs. In various embodiments, a receiving surface accommodates and contacts, by way of non-limiting examples, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more bandage packs. In some embodiments, a receiving surface accommodates two bandage packs. In some embodiments, a receiving surface accommodates one bandage pack.

A dispenser body has many suitable sizes. In various embodiments, a dispenser body is, for example, 10, 20, 30, 40, 50, 60, 70, 80, 90, 100, 200, 300, 400, 500, 600, 700, 800, 900, 1000 or more mm, including increments therein, in its largest dimension. In some embodiments, the size of a dispenser body is chosen to accommodate the size of a particular bandage and/or bandage pack. In other embodiments, the size of a dispenser body is chosen to accommodate placement or mounting in a particular location.

Referring to FIG. 1, in a particular embodiment, a dispenser body is designed to accommodate the two bandage packs. In this particular embodiment, the dispenser body is substantially 95.4 mm wide, 109.7 mm tall, and 10.0 mm deep. The dispenser body defines a rectangular, box-shaped interior and forms a substantially rectangular receiving surface. The receiving surface is substantially 91.6 mm wide and 104.6 mm tall.

Figure 10:
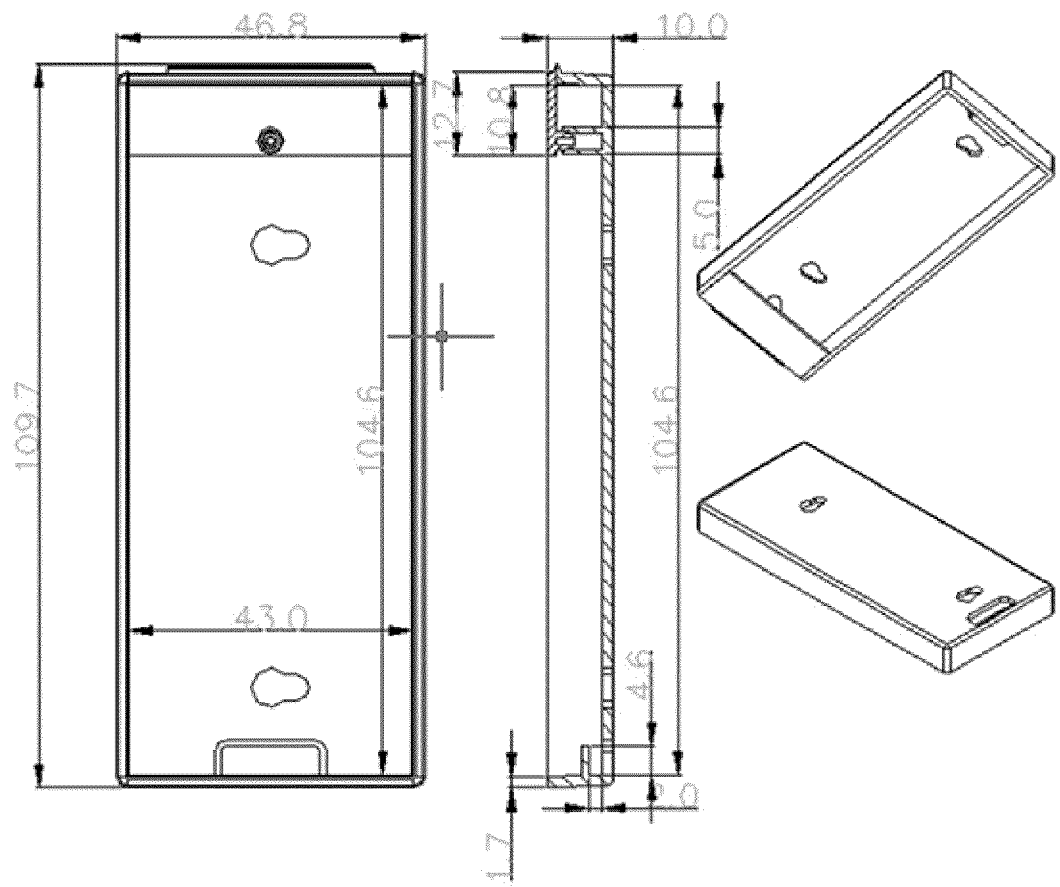
FIG. 10 shows multiple non-limiting views of an exemplary bandage dispenser; in this case, a bandage dispenser adapted to accommodate one bandage pack.

Referring to FIG. 10, in a particular embodiment, a dispenser body is designed to accommodate the one bandage pack. In this particular embodiment, the dispenser body is substantially 46.8 mm wide, 109.7 mm tall, and 10.0 mm deep. The dispenser body defines a rectangular, box-shaped interior and forms a substantially rectangular receiving surface. The receiving surface is substantially 43.0 mm wide and 104.6 mm tall.

Figure 6:
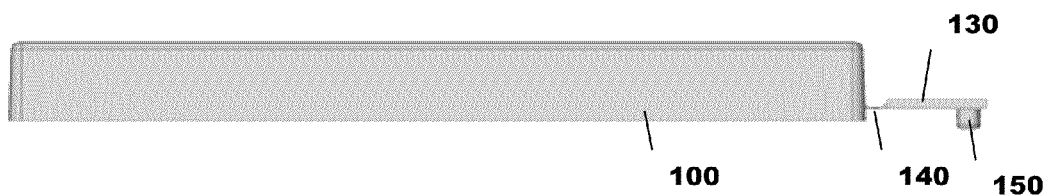
FIG. 6 is illustrative of a non-limiting exemplary side view of a bandage dispenser; in this case, a dispenser with a flap 130 hinged to a dispenser body 100 by a thin strip of flexible material 140.
Figure 7:
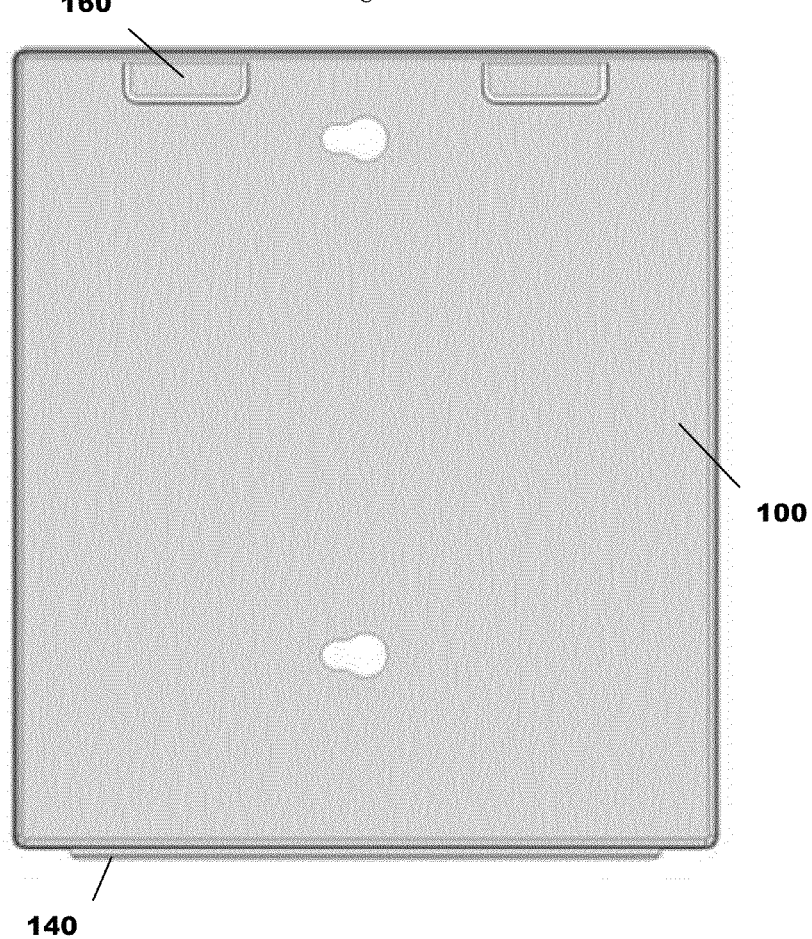
FIG. 7 is illustrative of a non-limiting exemplary reverse view of the bandage dispenser of FIG. 2; in this case, the flap is folded to overlay the receiving surface.
Figure 8:
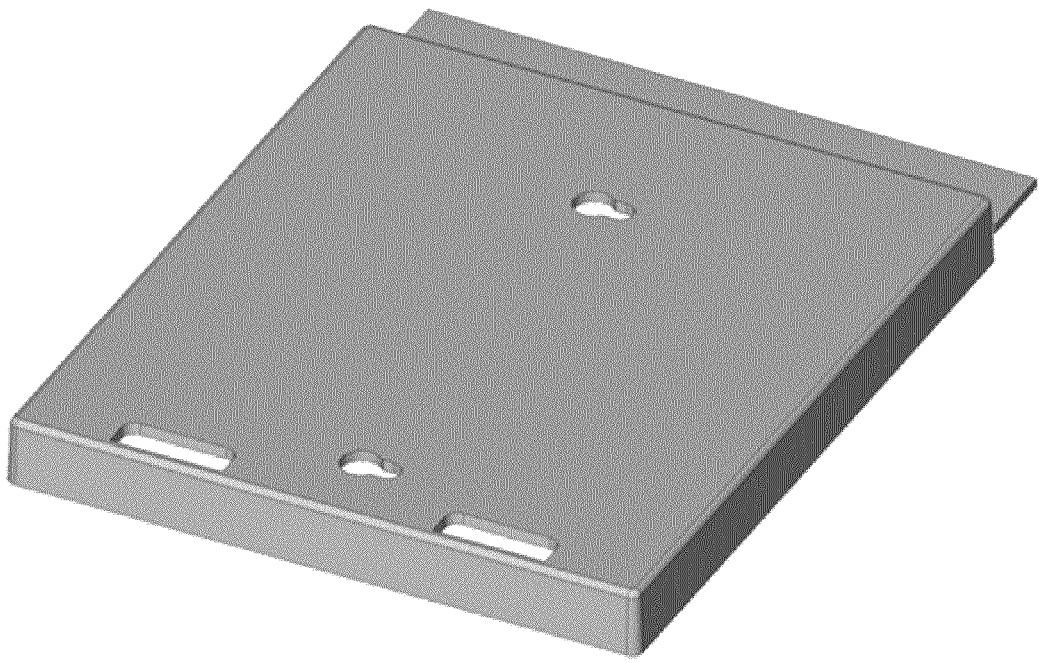
FIG. 8 is illustrative of a non-limiting exemplary reverse view of the bandage dispenser of FIG. 2; in this case, the hinged flap is unfolded.
Figure 9:
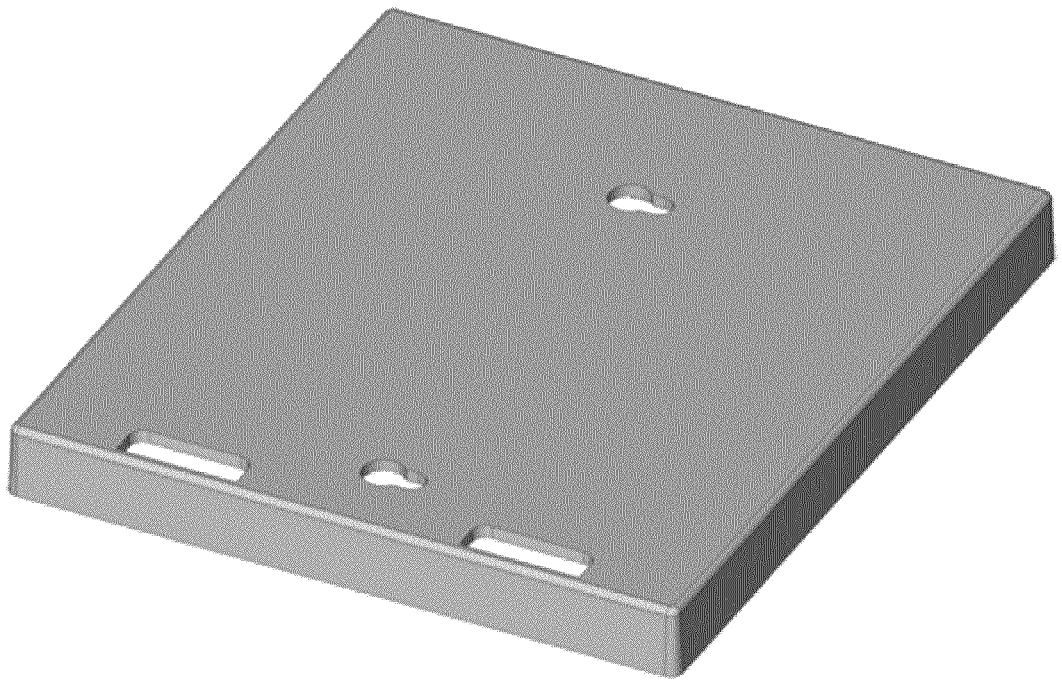
FIG. 9 is illustrative of a non-limiting exemplary reverse view of the bandage dispenser of FIG. 2; in this case, the hinged flap is folded to overlay the receiving surface and is not visible.

In some embodiments, a dispenser body includes one or more flaps. In further embodiments, a dispenser body is connected to one or more flaps by one or more hinges. Many types of hinges are suitable. In various embodiments, suitable hinges include, by way of non-limiting examples, a barrel hinge, a pivot hinge, and a continuous hinge. In some embodiments, a hinge is a sheet or strip of flexible material or a scored or perforated section of the dispenser body that is flexible such that the connection allows the flap to move (e.g., fold, pivot, bend, etc.). See e.g., FIG. 6. In some embodiments, a hinged flap is foldable to overlay a receiving surface. In further embodiments, a hinged flap overlays a receiving surface entirely. In other embodiments, a hinged flap overlays a receiving surface partially. In various embodiments, a dispenser body includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more flaps. In some embodiments, a dispenser body includes a flap corresponding to each bandage pack.

Figure 2:
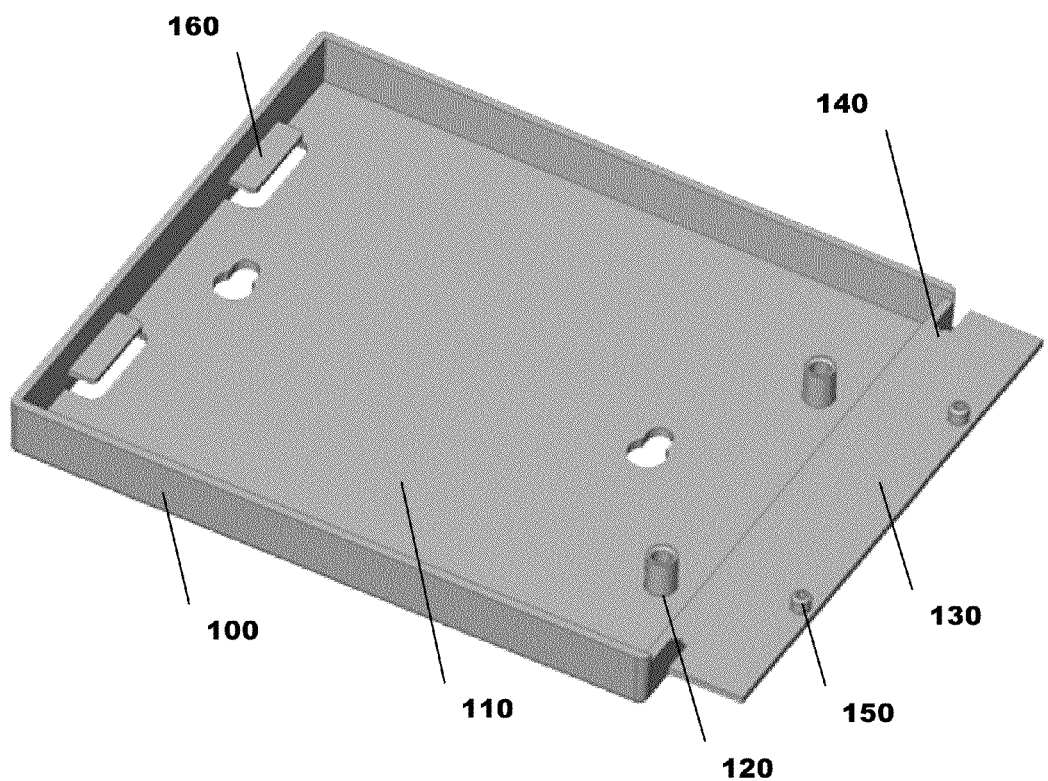
FIG. 2 shows a non-limiting example of a bandage dispenser; in this case, a bandage dispenser comprising a dispenser body 100, a receiving surface 110 with a pair of first retention elements 120, one hinged flap 130 with a pair of second retention elements 150, and a pair of third retention elements 160. In this case, the hinged flap is not folded to overlay the receiving surface and the first and second retention elements are not interlocked.
Figure 11:
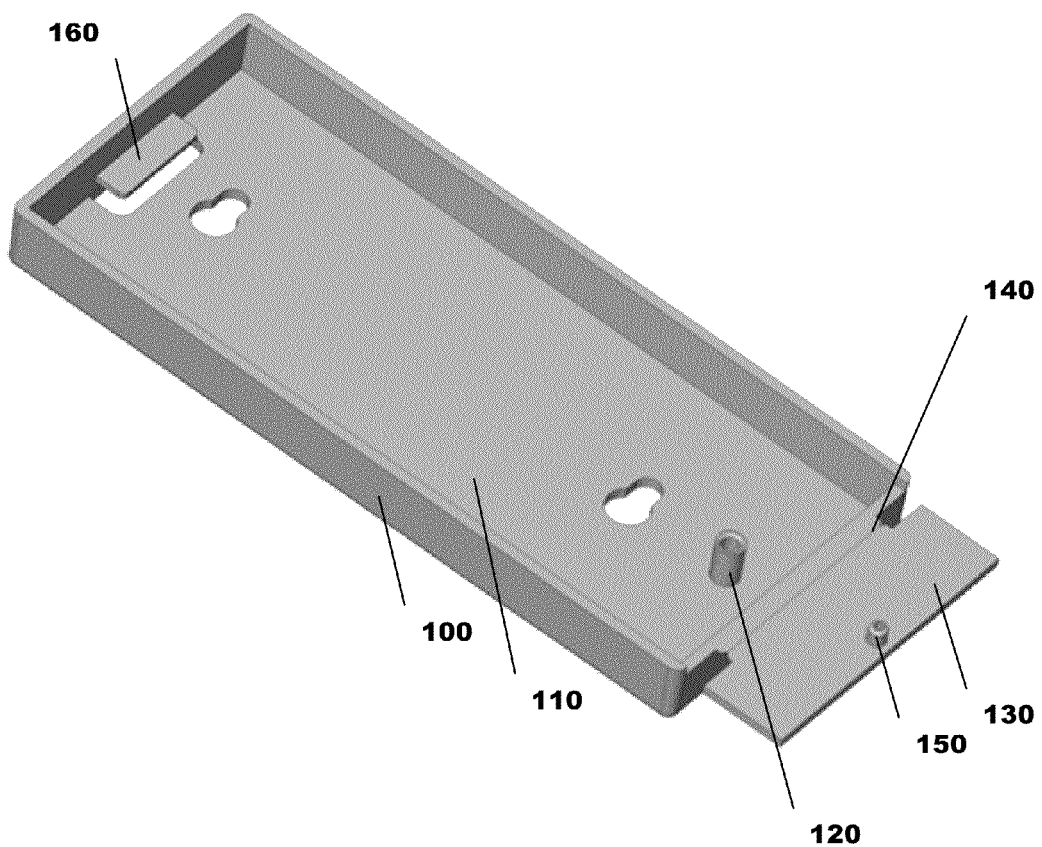
FIG. 11 is illustrative of a non-limiting example of a bandage dispenser; in this case, a bandage dispenser comprising a dispenser body 100, a receiving surface 110 with a first retention element 120, one hinged flap 130 with a second retention element 150, and a third retention element 160. In this case, the hinged flap is not folded to overlay the receiving surface and the first and second retention elements are not interlocked.

Referring to FIG. 2, in a particular embodiment, a dispenser body 100 including a receiving surface 110 is connected to a flap 130 by a thin, flexible section of material forming a hinge 140. See also, e.g., FIG. 11.

Figure 3:
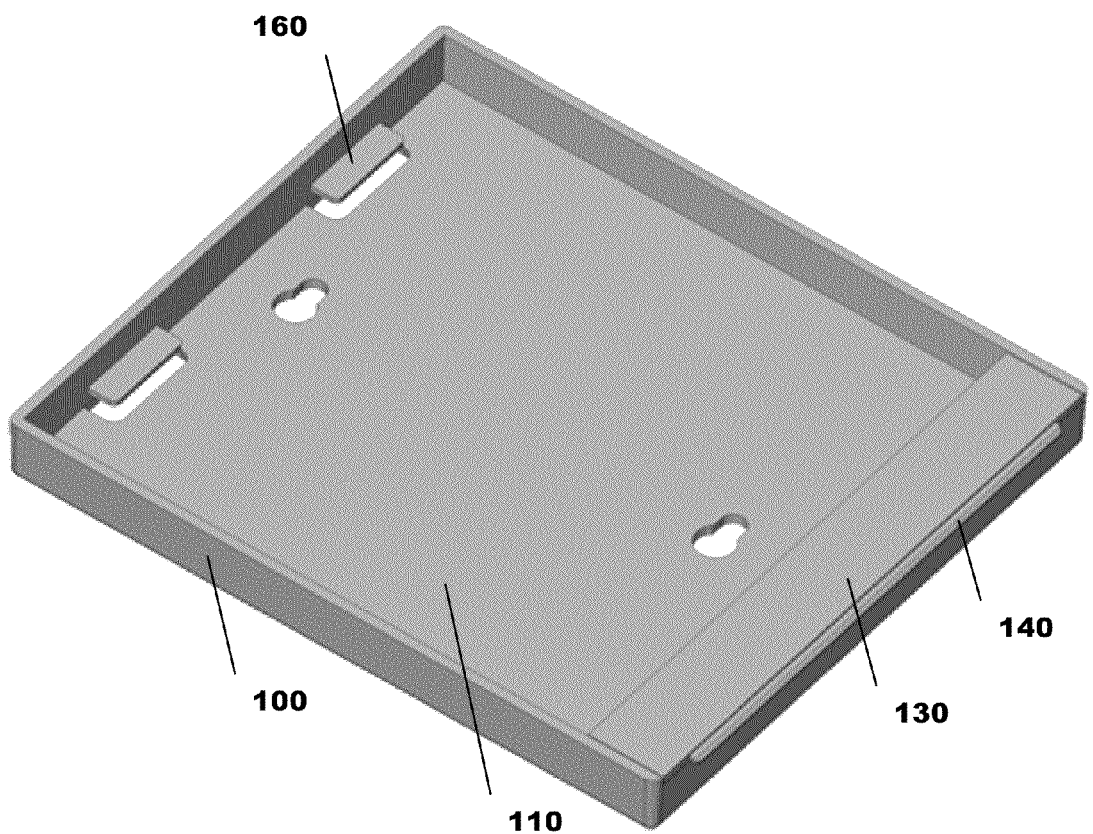
FIG. 3 is illustrative of a non-limiting exemplary configuration of the bandage dispenser of FIG. 2; in this case, the hinged flap 130 is folded to overlay the receiving surface 110 and the first and second retention elements are interlocked securing the flap in the folded position.
Figure 12:
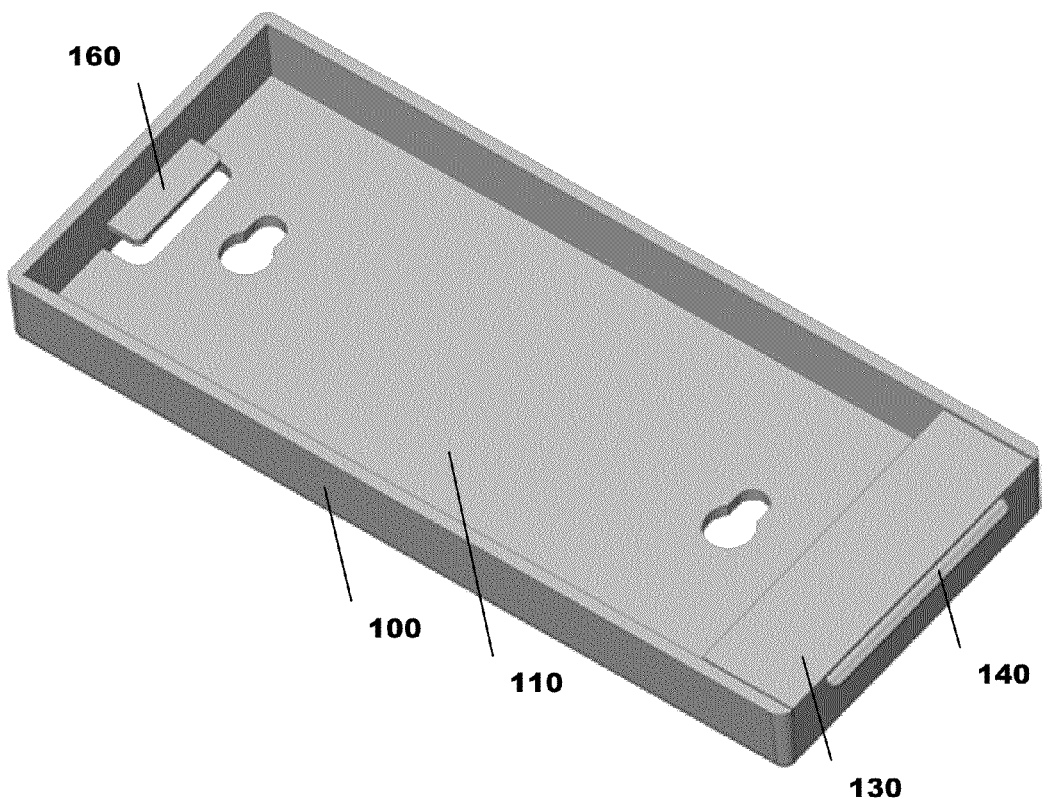
FIG. 12 is illustrative of a non-limiting exemplary configuration of the bandage dispenser of FIG. 11; in this case, the hinged flap 130 is folded to overlay the receiving surface 110 and the first and second retention elements are interlocked securing the flap in the folded position.
Figure 13:
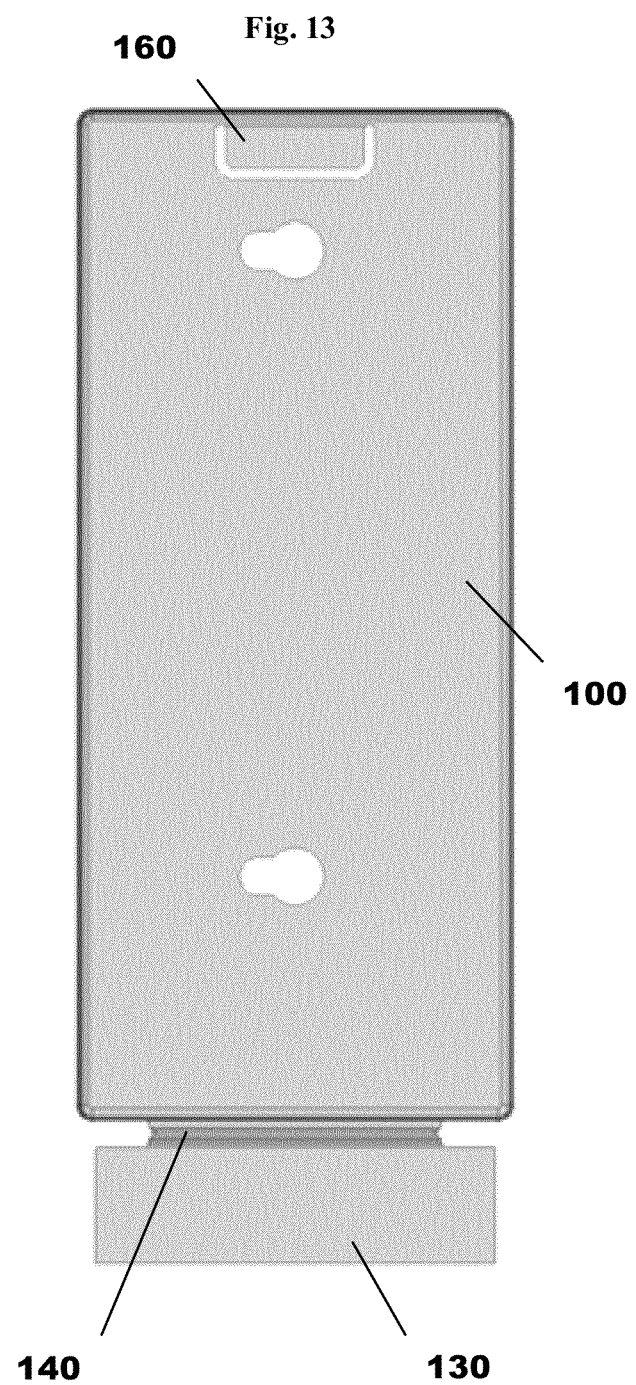
FIG. 13 is illustrative of a non-limiting exemplary reverse view of the bandage dispenser of FIG. 11; in this case, the hinged flap is unfolded.
Figure 14:
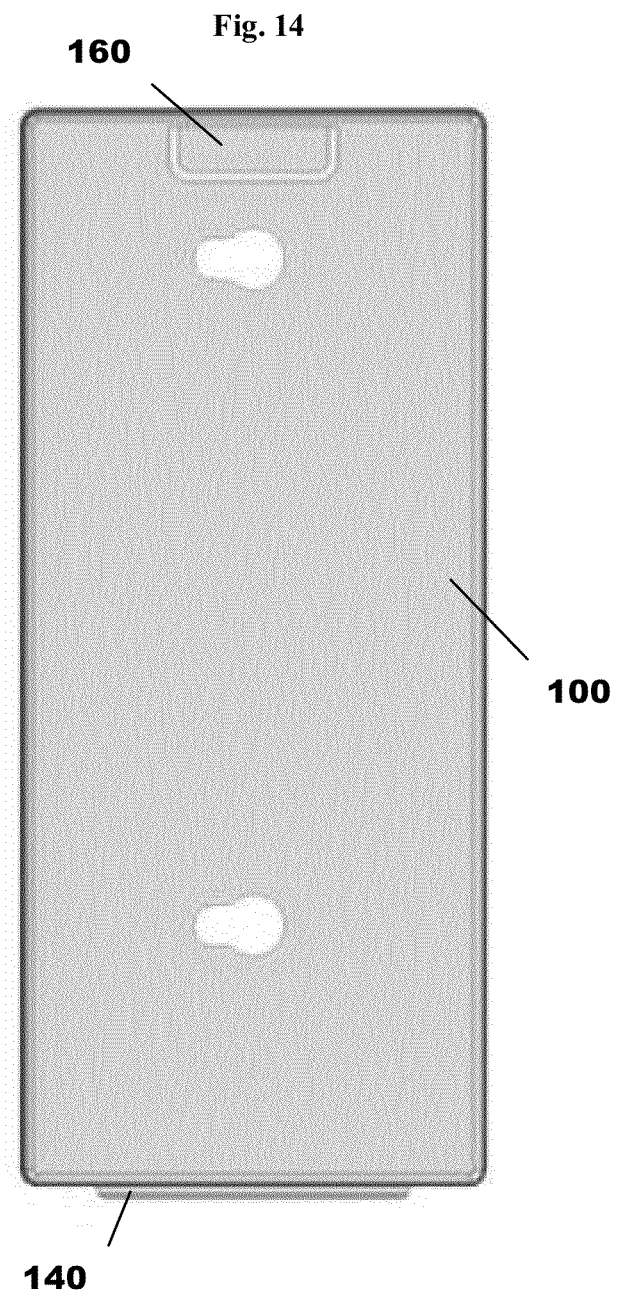
FIG. 14 is illustrative of a non-limiting exemplary reverse view of the bandage dispenser of FIG. 11; in this case, the hinged flap is folded to overlay the receiving surface and is not visible.
Figure 15:
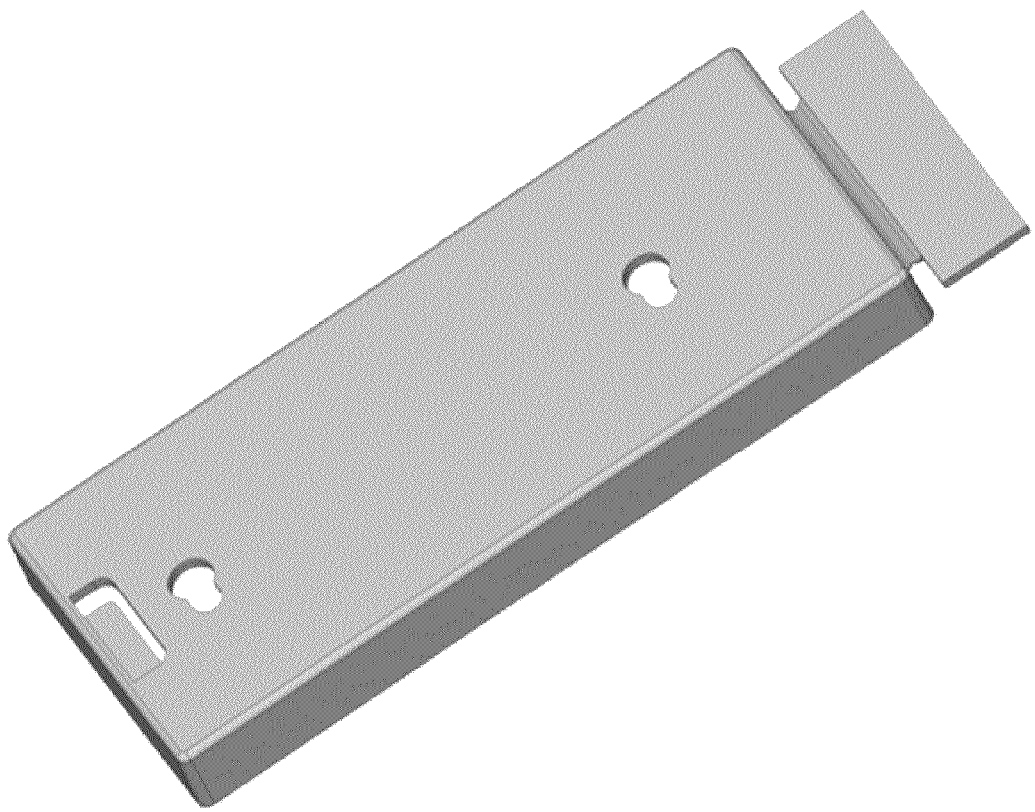
FIG. 15 is illustrative of another non-limiting reverse view of the bandage dispenser of FIG. 11; in this case, the hinged flap is unfolded.
Figure 16:
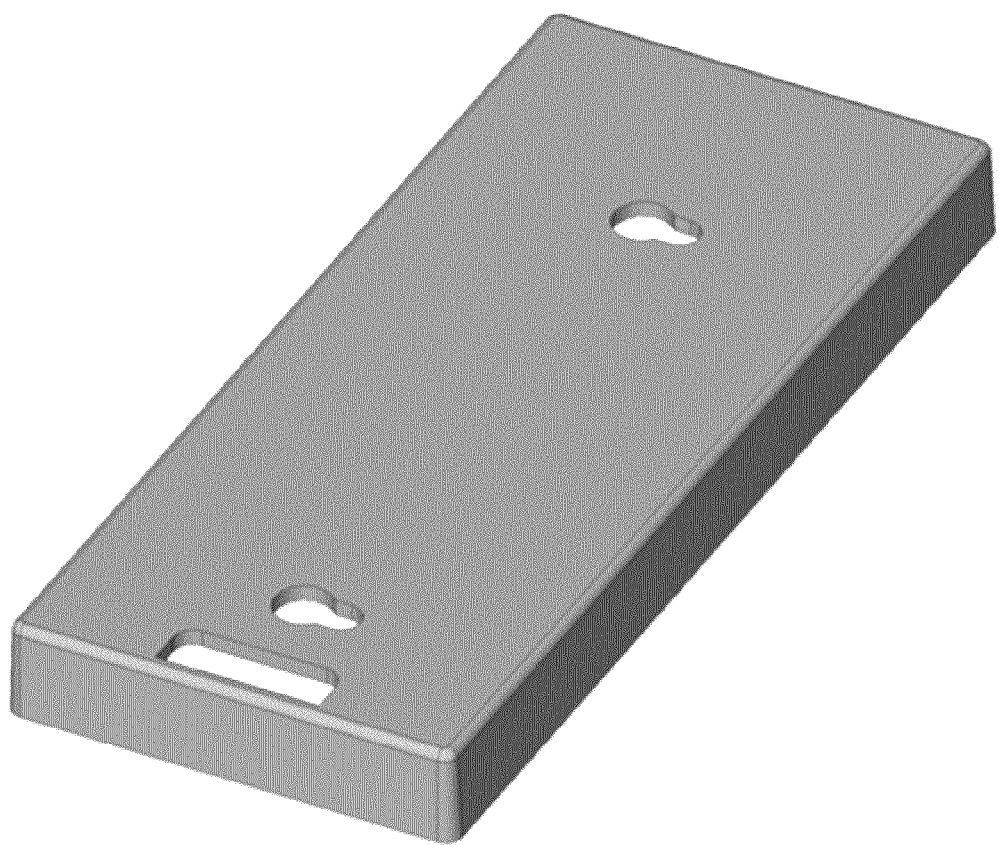
FIG. 16 is illustrative of another non-limiting reverse view of the bandage dispenser of FIG. 11; in this case, the hinged flap is folded to overlay the receiving surface and is not visible.

Referring to FIG. 3, in a particular embodiment, the dispenser body of FIG. 2 is depicted in an alternative configuration with a hinged flap 130 folded to overlay a portion of a receiving surface 110. See also, e.g., FIG. 12.

In some embodiments, a receiving surface includes one or more first retention elements. In various embodiments, a receiving surface includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more first retention elements. In some embodiments, one or more first retention elements interact with another retention element. In further embodiments, each first retention element interacts with a second retention element. In still further embodiments, each first retention element reversibly interlocks with a second retention element.

In some embodiments, a hinged flap includes one or more second retention elements. In various embodiments, a hinged flap includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more second retention elements. In some embodiments, one or more second retention elements interact with another retention element. In further embodiments, each second retention element interacts with a first retention element. In still further embodiments, each second retention element reversibly interlocks with a first retention element. In some embodiments, a dispenser body comprises one or more pairs of opposing retention elements such that when a hinged flap is folded to overlay a receiving surface, each first retention element aligns with and opposes a second retention element.

Many forms and designs are suitable for first and second retention elements. In various embodiments, first retention elements are, by way of non-limiting examples, snaps, clips, tabs, magnets, hook and loop fasteners, other fasteners, and the like, including combinations thereof. In some embodiments, first retention elements are protrusions from a receiving surface. In a particular embodiment, first retention elements are hollow tubular protrusions. In some embodiments, the form or design of a first retention element is chosen to allow for interaction, including reversible interlocking, with another retention element, such as a second retention element. Similarly, in various embodiments, second retention elements are, by way of non-limiting examples, snaps, clips, tabs, magnets, hook and loop fasteners, other fasteners, and the like, including combinations thereof. In some embodiments, second retention elements are protrusions from a hinged flap. In a particular embodiment, second retention elements are hollow tubular protrusions. In some embodiments, the form or design of a second retention element is chosen to allow for interaction, including reversible interlocking, with another retention element, such as a first retention element. In some embodiments, first and second retention elements are positioned such that each first retention element aligns with and opposes a second retention element when a hinged flap is folded to overlay a receiving surface. In further embodiments, an opposed pair of retention elements interlocks when, for example, one element of the pair fits into the other element of the pair.

Referring to FIG. 2, in a particular embodiment, a dispenser body 100 includes a receiving surface 110 including two first retention elements 120. In this embodiment, the first retention elements are hollow tubular protrusions from the receiving surface 110. Continuing to refer to FIG. 2, a dispenser body is connected to a flap 130 by a hinge 140. In this embodiment, a hinged flap 130 includes two second retention elements 150. Further in this embodiment, the second retention elements are tubular protrusions smaller than the first retention elements. Each first retention element aligns with and opposes a second retention element such that they form interlocking pairs when a hinged flap is folded to overlay a receiving surface. See also, e.g., FIG. 11.

Figure 4:
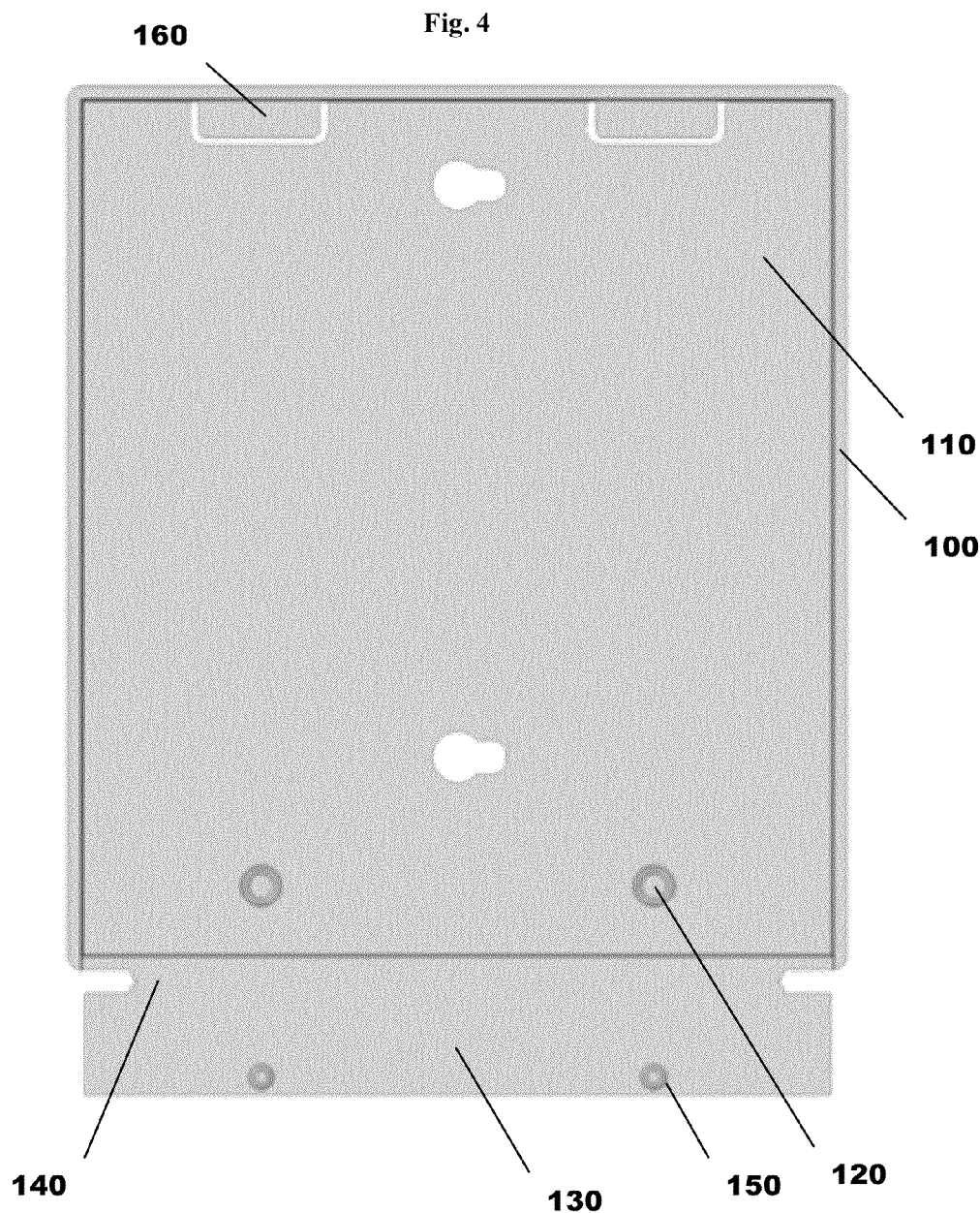
FIG. 4 is illustrative of a non-limiting exemplary frontal view of the bandage dispenser of FIG. 2.
Figure 5:
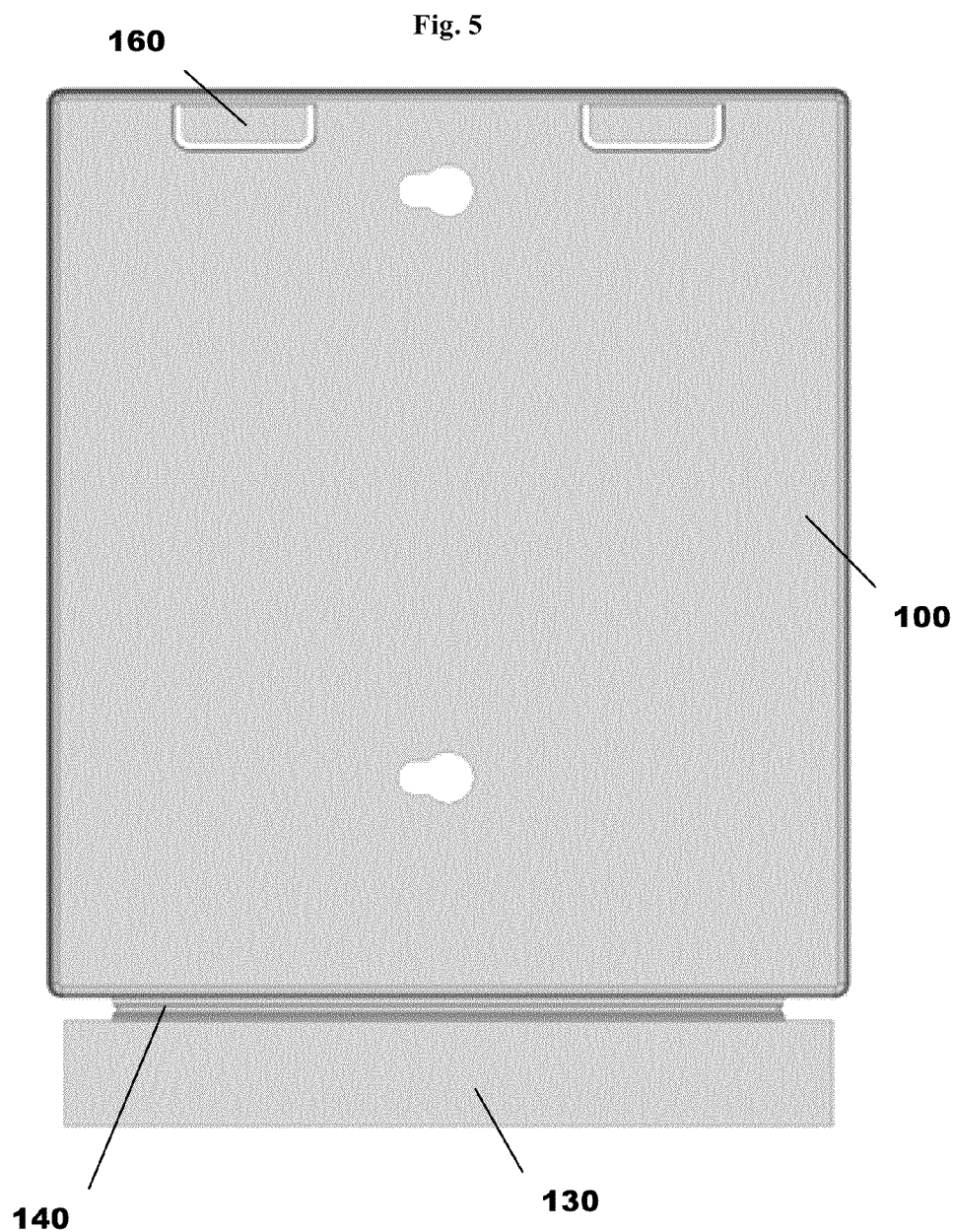
FIG. 5 is illustrative of a non-limiting exemplary reverse view of the bandage dispenser of FIG. 2.

Referring to FIG. 4, in a particular embodiment, the alignment of first retention elements 120 and second retention elements 150 is visible. In this particular embodiment, the first and second retention elements form opposing pairs that interlock when a flap 130 is folded about a hinge 140 to overlay a receiving surface 110.

FIG. 3 demonstrates a non-limiting configuration of a dispenser body wherein first and second retention elements (not visible) are interlocked to secure a hinged flap 130 in a folded position. See also, e.g., FIG. 12.

In some embodiments, a dispenser body in the folded configuration of FIGS. 3, 7, 9, 12, 14, and 16 secures one or more bandage packs onto a receiving surface. In some embodiments, a dispenser body secures one or more bandage packs onto a receiving surface by pressure, friction, adhesion, and the like, including combinations thereof. In further embodiments, a bandage pack is secured by a first retention element, a second retention element, or an interlocked pair of first and second retention elements passing through a bandage pack. In some embodiments, a retention element passes through a pre-formed opening in a bandage pack. In other embodiments, a retention element penetrates through a portion of a bandage pack when a hinged flap is folded to overlay a receiving surface, thus securing a bandage pack.

In some embodiments, a dispenser body includes one or more third retention elements. In further embodiments, one or more third retention elements are positioned on a dispenser body on a side opposite a hinged flap or on a side opposite first and second retention elements. In various embodiments, a dispenser body includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more third retention elements. In some embodiments, a dispenser body includes a third retention element corresponding to each bandage pack. In various embodiments, third retention elements are, by way of non-limiting examples, snaps, clips, tabs, magnets, hook and loop fasteners, other fasteners, and the like, including combinations thereof. In some embodiments, a third retention element interacts with one or more bandage packs. In further embodiments, a third retention element secures one or more bandage packs onto a receiving surface.

Again referring to FIG. 2, in a particular embodiment, a dispenser body 100 including a receiving surface 110 further includes two third retention elements 160. In this embodiment, each third retention element is a tab extending from a wall of a dispenser body parallel with a receiving surface 110. Further, in this embodiment, each third retention element interacts with a bandage pack to reversibly secure a bandage pack to a receiving surface. Also, a third retention element, for example, prevents a bandage pack from bending away from a dispenser body or receiving surface during removal of individual bandages. See also, e.g., FIGS. 3, 4, 5, and 7.

Again referring to FIG. 11, in a particular embodiment, a dispenser body 100 including a receiving surface 110 further includes one third retention element 160. In this embodiment, a third retention element is a tab extending from a wall of a dispenser body parallel with a receiving surface 110. Further, in this embodiment, a third retention element interacts with a bandage pack to reversibly secure a bandage pack to a receiving surface. Also, a third retention element, for example, prevents a bandage pack from bending away from a dispenser body or receiving surface during removal of individual bandages. See also, e.g., FIG. 12.

In light of the disclosure provided herein, the dispenser body, flaps, and retention elements are constructed from materials known to the manufacturing arts using techniques, tools, and machines known to the art. Suitable materials for the dispenser body, flaps, and retention elements are durable and rigid. Therefore, suitable materials include, by way of non-limiting examples, layered or corrugated paper, wood, plastic (e.g., polyethylene terephthalate, high-density polyethylene, polyvinyl chloride, polypropylene, high impact polystyrene, acrylonitrile butadiene styrene, and polyamide), metal (e.g., aluminum, steel, iron, nickel, titanium, zinc, and tin), carbon fiber, and combinations thereof. In some embodiments, the materials are opaque. In other embodiments, the materials are transparent. In some embodiments, the dispenser body includes a rear wall with features adapted to facilitate mounting the dispenser to a fixed surface. In further embodiments, features adapted to facilitate mounting include, by way of non-limiting examples, pre-drilled holes (see e.g., FIGS. 1-5, 7-16), adhesive, hook and loop fasteners, magnets, and suction cups.

Bandage Pack

In some embodiments, the methods, devices, and systems for dispensing individual bandages includes at least one bandage pack. In various embodiments, the system includes 2, 3, 4, 5, 6, 7, 8, 9, 10, 11, 12, 13, 14, 15, 16, 17, 18, 19, 20, 21, 22, 23, 24, 25, 26, 27, 28, 29, 30 or more bandage packs, including increments therein. In further embodiments, the system includes 2 bandage packs. In still further embodiments, the system includes 1 bandage pack. Bandages (also referred to as adhesive bandages, sticking plasters, and plasters) are small dressings often used to cover and protect minor to moderate injuries. In some embodiments, a bandage pack includes a rigid cover that is folded to enclose a plurality of individually wrapped bandages. In further embodiments, the individual bandages extend vertically beyond the upper edge of a cover such that the individual bandages are available to grasp and remove from the pack. In some embodiments, the individually wrapped bandages are bound to each other and to the cover, such that removal of an individual bandage from the pack causes the bound portion of the wrapper to be retained, thus freeing and partially exposing a bandage for application. In further embodiments, a free, partially exposed bandage is easily and rapidly applied to an injury with one hand. In some embodiments, individually wrapped bandages are bound to each other and to the cover along a bottom edge. In further embodiments, binding is accomplished, for example, by gluing, stapling, crimping, or melting the bandage pack cover and the individual bandages along a bottom edge.

In some embodiments, each bandage pack includes a pre-formed opening. In further embodiments, a pre-formed opening allows one or more elements of a bandage dispenser (e.g., retention elements, etc.) to pass through the pack. In still further embodiments, one or more elements of a bandage dispenser (e.g., retention elements, etc.) pass through a bandage pack to secure a pack to a receiving surface, thus retaining a pack in a dispenser. In other embodiments, each bandage pack includes a perforated, thin, or weakened area adapted to allow one or more elements of a bandage dispenser (e.g., retention elements, etc.) to be forced through a bandage pack to secure a pack to a receiving surface. In further embodiments, one or more elements of a bandage dispenser (e.g., retention elements, etc.) are forced through a bandage pack when a hinged flap is folded to overlay a portion of a receiving surface.

In various embodiments, each bandage pack includes 2, 3, 4, 5, 10, 15, 20, 25, 30, 35, 40, 45, 50 or more individually wrapped bandages, including increments therein. In some embodiments, each bandage pack comprises 5 to 40 individually wrapped bandages. In further embodiments, each bandage pack comprises 10 to 20 individually wrapped bandages. In various embodiments, individual bandage are fabric bandages, plastic bandages, washproof bandages, waterproof bandages, butterfly bandages, knuckle bandages, strip bandages (e.g., rectangular), and spot bandages (e.g., circular).

In some embodiments, more than one bandage pack is disposed in the interior compartment of the dispenser body and the packs are the same size. In other embodiments, more than one bandage pack is disposed in the interior compartment of the dispenser body and the packs are not the same size. In various embodiments, a bandage pack is 10, 15, 20, 25, 30, 35, 40, 45, 50, 55, 60, 65, 70, 75, 80, 85, 90, 95, 100 mm or more wide, including increments therein. In various embodiments, a bandage pack is 75, 80, 85, 90, 95, 100, 105, 110, 115, 120, and 125 mm high. In various embodiments, a bandage pack is 5, 10, 15, 20, 25, 30, 35, 40, 45, 50, 55, 60, 65, 70, 75, 80 mm or more deep, including increments therein. In further embodiments, a bandage pack has dimensions selected from: 72 mm wide×40 mm deep×107 mm long, 62 mm wide×40 mm deep×107 mm long, 60 mm wide×40 mm deep×107 mm long, 80 mm wide×27 mm deep×107 mm long, 80 mm wide×34 mm deep×107 mm long, and 80 mm wide× 40 mm deep×107 mm long. In some embodiments, the individually wrapped bandages have sizes selected from: 45 mm×51 mm, 40 mm×10 mm, 76 mm×38 mm, 76 mm×25 mm, and 76 mm×19 mm.

In light of the disclosure provided herein, a bandage pack and individually wrapped bandages are constructed from materials known to the manufacturing arts using techniques, tools, and machines known to the art. Suitable materials for a bandage pack cover include, by way of non-limiting examples, paper, cardstock, corrugated paper, and plastic (e.g., polyethylene terephthalate, high-density polyethylene, polyvinyl chloride, polypropylene, high impact polystyrene, acrylonitrile butadiene styrene, and polyamide). Suitable materials for a bandage are non-irritating, durable, and flexible and include, by way of non-limiting examples, textiles of natural fiber (e.g., cotton, linen, and hemp), textiles of synthetic fiber (e.g., nylon, polyester, aramid, olefin, and acrylic), and plastic (e.g., polyvinyl chloride, low-density polyethylene, and polypropylene). Suitable materials for a bandage wrapper are easily torn and include, by way of non-limiting examples, paper and waxed paper.

Figure 17:
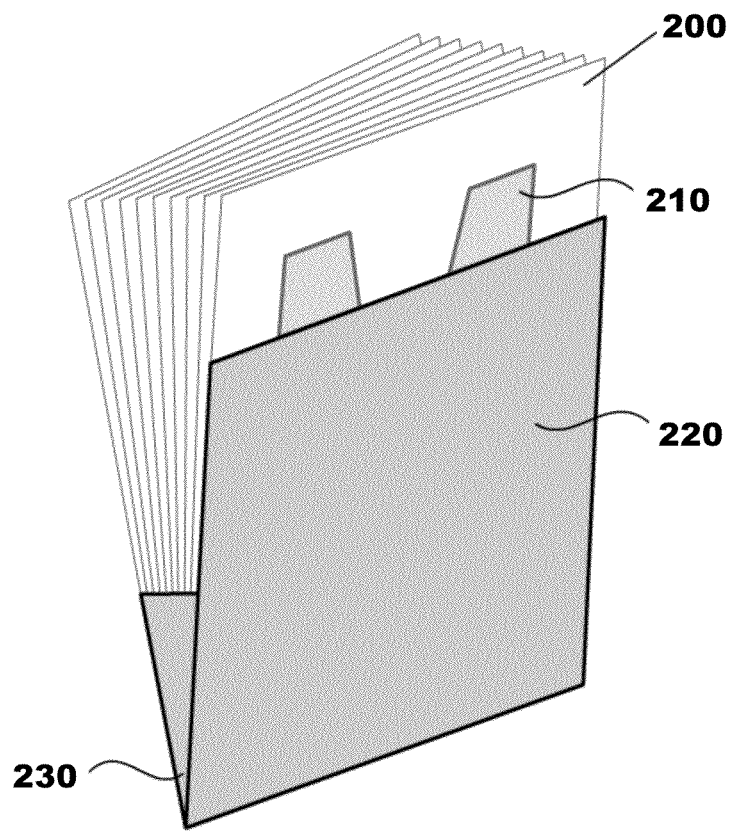
FIG. 17 is illustrative of a non-limiting example of a bandage pack; in this case, a bandage pack including a rigid cover 220 and a plurality of individually wrapped bandages 200. The bandages are bound to each other and to the cover along a bottom edge 230.

Referring to FIG. 17, in a particular embodiment, a bandage pack includes a cardstock cover 220 that is folded along a bottom edge 230 to enclose a plurality of individually wrapped knuckle bandages 210. The bandage wrapper 200 includes transparent material such that the individual bandage 210 is visible through the wrapper.

Figure 18:
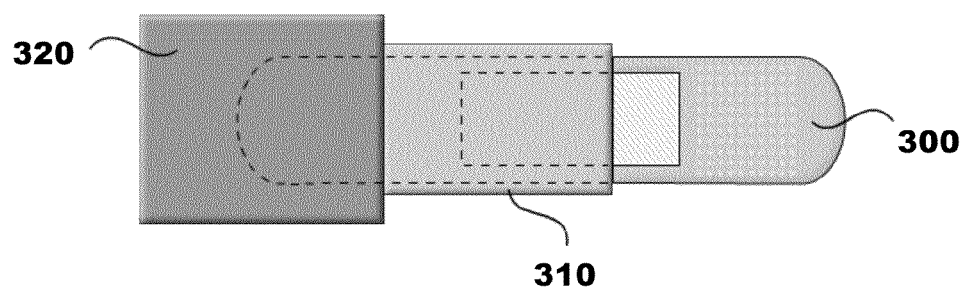
FIG. 18 is illustrative of a non-limiting example of an individually wrapped bandage; in this case, a bandage that has been removed from a bandage pack. Part of the wrapper 310 is retained in the bandage pack, thus partially exposing the bandage 300.

Referring to FIG. 18, in a particular embodiment, a strip bandage 300 is freed from a bandage pack and the bound portion of the wrapper is retained in the bandage pack such that only an unbound portion of the wrapper 310, 320 is associated with the bandage. In this freed and partially exposed state, the bandage 300 is available for easy and rapid application with one hand.

EXAMPLES

The following illustrative examples are representative of embodiments of the methods, devices, and systems for dispensing individual bandages described herein and are not meant to be limiting in any way.

Example 1

Manufacture of a Bandage Dispenser

The inventor of the instant application created a low cost bandage dispensing system design. The design included a bandage dispenser body and a plurality of disposable bandage packs, which each included individually wrapped bandages.

The dispenser body design specified a rectangular dispenser body with a substantially flat back wall forming a surface for receiving disposable bandage packs and four side walls. The walls of the dispenser were designed to be 1.7 mm thick. The back wall and side walls of the dispenser body defined an open box shaped interior space that was rectangular having dimensions of 91.6 mm width, 104.6 mm height, and 10.0 mm depth. The design of the dispenser body included a receiving surface with two integral first retention elements. The first retention elements were hollow and tubular in shape. The design of the dispenser body also included a flap attached to one edge of the body by a thin, flexible strip of material forming a hinge. The flap was designed to fold about the hinge to overlay the receiving surface. The hinged flap was designed to include two integral second retention elements positioned to align with the first retention elements when the flap was folded to overlay the receiving surface. The second retention elements were designed to fit snugly within the hollow of the first retention elements forming a reversible interlocking mechanism. When interlocked, the retention elements held the flap in a folded configuration. The design of the dispenser body also included two third retention elements on the wall of the dispenser body opposite the hinged flap. The third retention elements were designed as tabs of material extending from the dispenser body wall parallel to the receiving surface. The third retention elements were offset from the receiving surface by 2.0 mm. The back wall of the dispenser body was designed with two mounting holes to facilitate mounting the dispenser on a surface.

The bandage dispensing system also included several types of bandage packs. The bandage pack design included a rigid cover folded to enclose a plurality of individually wrapped bandages. The individual bandages were designed to extend vertically beyond the upper edge of the cover such that the individual bandages are available to grasp and remove from the pack. The design of the packs included individually wrapped bandages bound to each other and to the cover, such that removal of an individual bandage from the pack causes the bound portion of the wrapper to be retained, thus freeing and partially exposing a bandage for application. The packs were designed to fit into the interior space of the dispenser body in contact with the receiving surface. Each bandage pack was designed with a circular, pre-formed hole. The design specified that when a bandage pack was disposed on the receiving surface of the dispenser body, the first and second retention elements passed through the pre-formed hole when the hinged flap was folded to overlay the receiving surface. When the first and second retention elements were interlocked with each other, the bandage pack was secured within the dispenser body. The cover of each bandage pack slid under a third retention element, thus securing the opposite end of the pack as well.

The bandage dispenser was injection molded of nylon material according to the specifications of the design. Two bandage packs were secured within each bandage dispenser to form the assembled system.

Example 2

Use of a Bandage Dispenser

A 39-year-old male cuts the thumb of his left hand while chopping vegetables in his home kitchen. He has previously placed three separate bandage dispensers in his home, one in his garage, one in his bathroom, and another in his kitchen pantry. When he realizes that he his injured, he uses a clean paper towel to apply pressure for one minute in order to slow the bleeding. Subsequently, he reaches for a bandage to cover and protect the wound as well as to further control bleeding. He grasps an individually wrapped strip bandage, which is bound in a bandage pack. Each individually wrapped bandage is bound to the others in the pack and to a moderately rigid bandage pack cover. The wrapper of each bandage is scored such that removal of an individual bandage from the pack causes the bound portion of the wrapper to be retained, freeing and partially exposing the bandage. The pack is further secured within a nylon bandage dispenser (manufactured as described in Example 1), which is mounted to the wall of his pantry.

When the man pulls upward on the individual, wrapped bandage, the mounted dispenser retains the bandage pack. The resulting force separates the bandage wrapper, freeing a partially unwrapped bandage, cleanly and ready for application. The bound portion of the wrapper is retained in the bandage pack. He applies the bandage to his injured thumb.

Example 3

Refilling of a Bandage Dispenser

Three days after the events described in Example 2, the injured man decides to replace the partially depleted bandage pack which he and other members of his family have used several times. To refill the bandage dispenser (manufactured as described in Example 1), he grasps the folded, hinged flap on the front of the mounted dispenser and pulls outward (e.g., toward himself) and downward. The first and second retention elements disengage and the flap folds (e.g., rotates about the hinge) downward, away from the receiving surface of the dispenser. The man next pulls the depleted bandage pack outward, away from the receiving surface, which removes the first retention element from the pre-formed opening in the bandage pack. He finally pulls the cover of the depleted bandage pack downward and outward to free it from under the third retention element.

He places a new bandage pack into the bandage dispenser, thus refilling the system. To do this, he slips the top edge of the bandage pack cover under the tab of the third retention element and pushes the hollow tube of the first retention element through the pre-formed opening at the bottom of the bandage pack. He then folds (e.g., rotates) the flap about the hinge so that it overlays the bandage pack and the receiving surface of the dispenser. He presses firmly on the folded flap to force the second retention elements on the hinged flap into the hollows of the first retention elements on the receiving surface, securing the bandage pack within the bandage dispenser.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for dispensing bandages comprising:
   a. a dispenser body comprising a receiving surface with a first retention element and a hinged flap with a second retention element, wherein the hinged flap is foldable to overlay at least a portion of the receiving surface; and
   b. at least one bandage pack disposed on said receiving surface, wherein each bandage pack comprises at least one individually wrapped bandage, wherein the first retention element, the second retention element, or both pass through at least one of said at least one bandage pack;
   provided that when the hinged flap is folded to overlay said receiving surface, the first retention element reversibly interlocks with the second retention element thus securely retaining said at least one bandage pack.

2. The system of claim 1, wherein said first and second retention elements cooperate to define one or more pairs of opposing retention elements such that when a hinged flap is folded to overlay the receiving surface, each first retention element aligns with and opposes a second retention element.

3. The system of claim 2, comprising one to ten pairs of opposing retention elements.

4. The system of claim 3, comprising one or two pairs of opposing retention elements.

5. The system of claim 3, wherein at least one pair of opposing retention elements passes through at least one bandage pack.

6. The system of claim 1, comprising one to ten bandage packs.

7. The system of claim 6, comprising one or two bandage packs.

8. The system of claim 6, comprising a hinged flap corresponding to each bandage pack.

9. The system of claim 1, wherein each bandage pack comprises three to fifty individually wrapped bandages.

10. The system of claim 1, wherein each bandage pack comprises one or more pre-formed openings for passage of one or both of the first retention element and the second retention element.

11. A system for dispensing individual bandages comprising:
   a. a dispenser body comprising:
      i. a substantially rectangular receiving surface with one or more first retention elements;
      ii. a hinged flap with one or more second retention elements, wherein the hinged flap is foldable to overlay at least a portion of the receiving surface such that each first retention element aligns with and opposes a second retention element;
      iii. one or more third retention elements on a side opposite the hinged flap;
   b. one or more bandage packs disposed on said receiving surface, wherein each said bandage pack comprises a plurality of individually wrapped bandages, wherein removal of an individual bandage from said pack causes a portion of a wrapper to be retained, thus freeing and partially exposing the bandage;
   provided that when the hinged flap is folded to overlay the receiving surface each first retention element passes through one or more of said one or more bandage packs and reversibly interlocks with an aligned one of said one or more second retention elements.

12. The system of claim 11, comprising one to ten pairs of opposing retention elements.

13. The system of claim 11, comprising one to ten bandage packs.

14. The system of claim 11, wherein each bandage pack comprises one or more pre-formed openings for passage of at least one of said one or more first retention elements, said one or more second retention elements, or both.

15. A bandage dispenser comprising:
   a. a substantially flat bandage pack receiving surface with one or more first retention elements protruding from the receiving surface; and
   b. a hinged flap with one or more second retention elements, wherein the hinged flap is foldable to overlay at least a portion of the receiving surface such that each first retention element aligns with, opposes, and reversibly interlocks with an aligned one of said one or more second retention elements.

16. The bandage dispenser of claim 15, further comprising one or more third retention elements on a side opposite the hinged flap.

17. The bandage dispenser of claim 15, wherein said first and second retention elements are adapted to retain one or more bandage packs by passing through an opening in each pack.

18. The bandage dispenser of claim 15, comprising one to ten pairs of opposing first and second retention elements.

19. The bandage dispenser of claim 18, comprising one or two pairs of opposing first and second retention elements.

* * * * *